(12) United States Patent
Breunissen et al.

(10) Patent No.: US 6,912,481 B2
(45) Date of Patent: Jun. 28, 2005

(54) MEDICAL EQUIPMENT PREDICTIVE MAINTENANCE METHOD AND APPARATUS

(75) Inventors: John R. Breunissen, Wauwatosa, WI (US); Kallahalli R. Shubha, Pewaukee, WI (US); Christopher C. Hardiman, Waukesha, WI (US)

(73) Assignee: GE Medical Systems, Inc., Pewaukee, WI (US)

( * ) Notice: Subject to any disclaimer, the term of this patent is extended or adjusted under 35 U.S.C. 154(b) by 83 days.

(21) Appl. No.: 10/388,872

(22) Filed: Mar. 14, 2003

(65) Prior Publication Data

US 2004/0181368 A1 Sep. 16, 2004

(51) Int. Cl.[7] .............................................. G06F 11/30
(52) U.S. Cl. ...................... 702/184; 702/182; 702/183; 702/185; 702/189
(58) Field of Search ............................... 702/179–189; 378/4, 8, 117, 118, 98, 207; 382/131, 128; 709/201, 227, 203; 600/425, 410

(56) References Cited

U.S. PATENT DOCUMENTS

| | | | | |
|---|---|---|---|---|
| 4,853,946 A | * | 8/1989 | Elliott et al. ................... 378/4 |
| 6,691,064 B2 | * | 2/2004 | Vroman ...................... 702/183 |
| 2002/0031086 A1 | * | 3/2002 | Welin ......................... 370/229 |
| 2002/0152395 A1 | * | 10/2002 | Zhang et al. ............... 713/200 |
| 2002/0152400 A1 | * | 10/2002 | Zhang et al. ............... 713/201 |
| 2002/0161990 A1 | * | 10/2002 | Zhang et al. .................. 713/1 |
| 2002/0188652 A1 | * | 12/2002 | Goldhaber et al. ......... 709/201 |
| 2002/0198997 A1 | * | 12/2002 | Linthicum et al. ......... 709/227 |
| 2003/0156683 A1 | * | 8/2003 | Adachi ....................... 378/117 |
| 2003/0181804 A1 | * | 9/2003 | Gagnon et al. ............. 600/410 |
| 2003/0215125 A1 | * | 11/2003 | Yokoi et al. ................ 382/131 |
| 2004/0138920 A1 | * | 7/2004 | Sawanaga et al. ............. 705/2 |
| 2005/0024695 A1 | * | 2/2005 | Prakash ...................... 358/504 |

* cited by examiner

*Primary Examiner*—Carol S. W. Tsai
(74) *Attorney, Agent, or Firm*—Fletcher Yoder

(57) ABSTRACT

A technique for scheduling planned maintenance of equipment, such as medical imaging systems, permits selection of time-based or usage-based scheduling. If usage-based scheduling is selected, operational data collected from the systems serves as the basis for computing a maintenance schedule along with reference usage values for parameters indicative of use. Reference may be made to norms for similar equipment, and the schedule may be adapted accordingly. Trends in usage, increasing or decreasing, may be accommodated by comparison of the usage determinations over time, and schedules may be adjusted accordingly.

24 Claims, 8 Drawing Sheets

FIG. 7

MEDICAL EQUIPMENT PREDICTIVE MAINTENANCE METHOD AND APPARATUS

BACKGROUND OF THE INVENTION

The present invention relates generally to medical equipment maintenance and, more particularly, to a technique for automatically scheduling maintenance sessions based upon usage data, and modifying set schedules based upon changing usage data.

In the field of medical equipment, particularly diagnostic equipment such as imaging systems, regular maintenance is important to provide a continuing high degree of reliability and operability. Imaging equipment, for example, may require periodic servicing of components that may wear, be consumed, or become uncalibrated. It is common in the field of medical equipment servicing to provide for both "as needed" servicing (i.e. in response to service requests), and for regular servicing to ensure optimum performance and efficiency of equipment throughout medical institutions.

Current approaches to servicing medical equipment include regularly timed service calls, typically based upon contractual arrangements between service providers and medical institutions. The providers commonly schedule either on-site service visits or remote servicing, or both, on a regular timed basis. The intervals between such visits are generally determined in rather empirical fashions, however, and may vary widely between service providers, institutions, contracts, regions, and so forth, even for similar types of equipment.

There is a need in the field of medical equipment servicing for an improved technique for scheduling service to specific equipment components and types of equipment that would be more closely coupled to the actual need for servicing. There is a particular need for a technique that would permit automatic scheduling based upon some criteria or criterion other than simple time intervals, or that would allow for selection between such interval-based servicing and the need-based approach.

BRIEF DESCRIPTION OF THE INVENTION

The present technique provides a novel technique for scheduling servicing of medical equipment designed to respond to such needs. The technique is applicable to a wide range of equipment, but is particularly well suited to sensitive and specialized equipment, such as diagnostic imaging systems. It should be noted, however, that the technique, applied to such systems, may find utility outside the medical field, such as in such areas as part inspection, baggage inspection, quality control, and so forth.

In accordance with a first aspect of the invention, a method for scheduling maintenance of imaging systems is provided. The method includes steps for accessing operational data collected from an imaging system, and identifying a trend in usage of the system based upon the operational data and updating usage data based upon the identified trend. The method then provides for calculating a planned maintenance schedule based upon the usage data and upon a reference usage value.

In accordance with another aspect of the invention, a method is provided for scheduling maintenance of imaging systems that first permits selecting time-based or usage-based planned maintenance scheduling. If time-based scheduling is selected, a maintenance schedule is computed based upon a desired maintenance interval. If usage-based scheduling is selected, usage data for an imaging system is accessed, and a planned maintenance schedule is calculated based upon the usage data and upon a reference usage value.

In accordance with a further aspect of the invention, a method is provided for scheduling planned maintenance for imaging systems, in which steps are provided for collecting operational data from a plurality of imaging systems via a network, and converting the operational data to usage data for parameters of interest. A usage-based planned maintenance schedule is then calculated for each imaging system based upon the respective usage data and respective reference usage values for the parameters of interest.

Systems and computer programs that afford functionality of the type defined by such methods are also provided by the present technique.

BRIEF DESCRIPTION OF THE DRAWINGS

FIG. 7 is a representation of an exemplary display or interface page as may be used in conjunction with the present maintenance scheduling technique.

DETAILED DESCRIPTION OF SPECIFIC EMBODIMENTS

Figure 1:
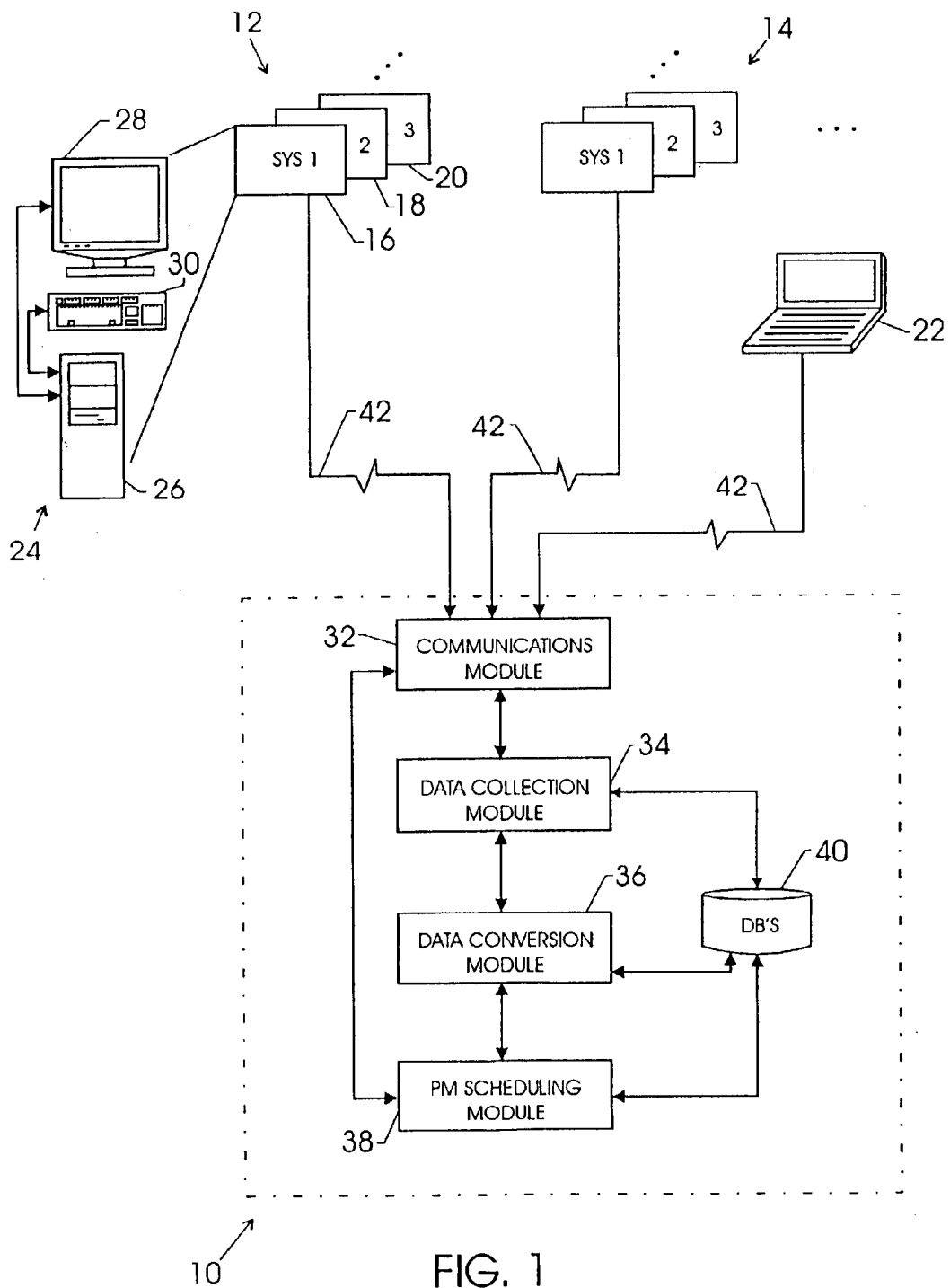
FIG. 1 is a diagrammatical representation of an exemplary planned maintenance scheduling system in accordance with aspects of the present technique.

Turning now to the drawings, and referring first o FIG. 1, a planned maintenance scheduling system is illustrated and designated generally by the reference numeral 10. While the system may be utilized to provide scheduled maintenance to a wide range of equipment, it is particularly well suited to providing remotely coordinated servicing of medical equipment, such as medical diagnostic systems. Such systems, and diagnostic imaging systems in particular, are associated with unique problems due to their complexity and the extreme demands made on reliability and availability. Such challenges are addressed in the present technique, in accordance with aspects of which planned maintenance is automatically scheduled on either a timed basis or a usage basis, with usage-based parameters being collected remotely. Moreover, as described in greater detail below, the usage scheduling aspects of the technique permit recasting of maintenance schedules as a function of changing usage, thereby avoiding unnecessary maintenance while ensuring that maintenance is customized by the actual rate of usage of the equipment.

In the embodiment of FIG. 1, the system is illustrated as being linked to two groups or institutions 12 and 14 which may be geographically remote from one another. Additional groups may, of course, be similarly linked to the system. Each group, in turn, includes a range of equipment, designated as systems 16, 18 and 20. The individual equipment systems may also be remote from one another, such as at different physical locations in an institution, in different departments, on different floors, and so forth. Data is collected from the equipment, as discussed below, and utilized by system 10 for scheduling planned maintenance of the equipment and components thereof. Also coupled to the system 10 is a field engineer's station 12, such as a personal computer, portable computer, personal digital assistant, or the like. The station 12 allows field engineers to view and coordinate servicing of the equipment, change schedules, set scheduling parameters, and so forth as discussed below.

Each system 16, 18, 20 will typically include an operator interface station 24. The operator interface station, which may also control some or all of the functions of the equipment, may also be used to view maintenance schedules on system 10. In general, such interface stations will include one or more general purpose or application specific computers 26, including memory for storing data collection routines and the resulting data that can be accessed by system 10. Such data may also, of course, be stored within each equipment system 16, 18, 20 and accessed directly therefrom. Each system interface station 24 will also include a monitor 28 for may be used for viewing interface pages on system 10, as described below, and input devices 30 for interacting with the computer and system. In a present configuration, station 22 may provide a primary means for accessing the scheduling data described below, while systems 16, 18 and 20 provide an optional or supplemental means for access and viewing the data.

System 10 includes a number of components associated to carry out the functionality described below. Such components may comprise any suitable computer hardware, software or firmware, including elements located at a single location and elements widely dispersed from one another. In a present embodiment, system 10 includes a network of components configured to exchange data with systems 16, 18, 20 of various groups 12 and 14 via a communications modules, represented generally at reference numeral 32. As will be appreciated by those skilled in the art, any suitable circuitry, such as modems, servers, firewalls, VPN's and so forth may be included in such modules. A data collection module 34 coordinates acquisition of relevant data from the systems 16, 18, 20 for planning maintenance. Such data may include various operational parameters of the systems, which will vary depending upon the equipment type, the manufacturer, the physical nature of the operation of the equipment, and so forth. The data collection module 34 will typically identify what data is desired for each piece of equipment for which maintenance is scheduled, as well as where and how to identify the data in the system and extract it for processing.

A data conversion module 36 performs any conversion of the collected data that may be required to scheduling purposes. For example, as described more fully below, collected data may include raw, partially processed or processed data, and may represent various parameters of the equipment. When planned maintenance is to be performed on a usage basis, indications of the degree of usage, and therefore the appropriate timing for maintenance, may be provided by the collected data itself, or by data derived from the collected data. By way of example, as described below, maintenance of a CT imaging system may be appropriately scheduled based upon revolutions of a gantry assembly, while collected data may reflect more fundamental data that is present in the CT system and that can be related to gantry revolutions by know relationships programmed into the conversion module 36.

A planned maintenance scheduling module 38 performs the desired scheduling. Various algorithms may be implemented by the scheduling module, and in a present embodiment, maintenance may be scheduled based simply upon time intervals or upon actual usage of the maintained systems or of components of the systems. The schedules, along with collected data, system identifying data, and other data, may then be stored within a suitable memory, as represented by reference numeral 40 in FIG. 1. The entire system 10 may then communicate with the various maintained systems via links to a network 42, over which it may transmit schedules and collect the data required for scheduling maintenance.

As mentioned above, the present technique is particularly well suited for scheduling planned maintenance for complex medical equipment, such as medical diagnostic imaging systems. FIGS. 2–6 illustrate generic and certain specific modalities of imaging equipment with which the system may be implemented. It should be borne in mind, however, that the imaging equipment may be used in contexts other than the medical field, such as in part inspection, baggage handling and inspection, quality control, and so forth.

Figure 2:
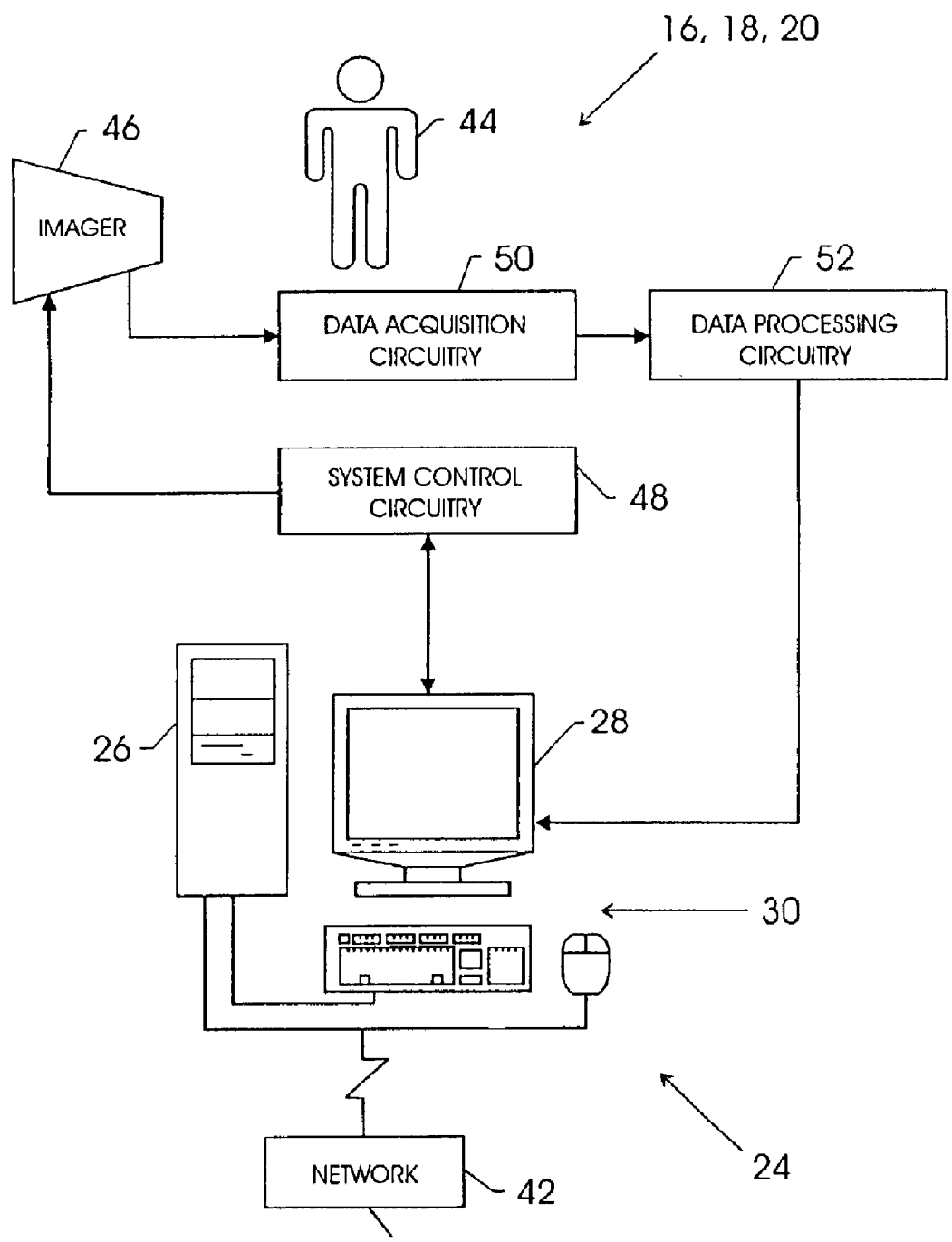
FIG. 2 is a general diagrammatical representation of certain functional components of an exemplary generic imaging system equipped for scheduling of planned maintenance via the present technique.

In the medical diagnostic context, various imaging resources may be available for diagnosing medical events and conditions in both soft and hard tissue, and for analyzing structures and function of specific anatomies. All such resources may be integrated into the present technique for automated planned maintenance scheduling. Moreover, imaging systems are available which can be used during surgical interventions, such as to assist in guiding surgical components through areas which are difficult to access or impossible to visualize. FIG. 2 provides a general overview of an exemplary imaging system, while FIGS. 3–6 offer somewhat greater detail into the major system components of certain specific modality systems.

Referring to FIG. 2, an imaging system 16, 18, 20 generally includes some type of imager 46 which detects signals and converts the signals to useful data. As described more fully below, the imager 46 may operate in accordance with various physical principles for creating the image data. In general, however, image data indicative of regions of interest in a patient 44 are created by the imager either in a conventional support, such as photographic film, or in a digital medium.

The imager operates under the control of system control circuitry 48. The system control circuitry may include a wide range of circuits, such as radiation source control circuits, timing circuits, circuits for coordinating data acquisition in conjunction with patient or table of movements, circuits for controlling the position of radiation or other sources and of detectors, and so forth. The imager 46, following acquisition of the image data or signals, may process the signals, such as for conversion to digital values, and forwards the image data to data acquisition circuitry 50. In the case of analog media, such as photographic film, the data acquisition system may generally include supports for the film, as well as equipment for developing the film and producing hard copies that may be subsequently digitized. For digital systems, the data acquisition circuitry 50 may perform a wide range of initial processing functions, such as adjustment of digital dynamic ranges, smoothing or sharpening of data, as well as compiling of data streams and files, where desired. The data is then transferred to data processing circuitry 52 where additional processing and analysis are performed. For conventional media such as photographic film, the data processing system may apply textual information to films, as well as attach certain notes or patient-identifying information. For the various digital imaging systems available, the data processing circuitry perform substantial analyses of data, ordering of data, sharpening, smoothing, feature recognition, and so forth.

Ultimately, the image data is forwarded to some type of operator interface 24 for viewing and analysis. While operations may be performed on the image data prior to viewing, the operator interface 24 is at some point useful for viewing reconstructed images based upon the image data collected. It should be noted that in the case of photographic film, images are typically posted on light boxes or similar displays to permit radiologists and attending physicians to more easily read and annotate image sequences. The images may also be stored in short or long term storage devices, for the present purposes generally considered to be included within the interface 24, such as picture archiving communication systems. The image data can also be transferred to remote locations, such as via network 42. It should also be noted that, from a general standpoint, the operator interface 24 affords control of the imaging system, typically through interface with the system control circuitry 48. Moreover, it should also be noted that more than a single operator interface 24 may be provided. Accordingly, an imaging scanner or station may include an interface which permits regulation of the parameters involved in the image data acquisition procedure, whereas a different operator interface may be provided for manipulating, enhancing, and viewing resulting reconstructed images.

The following is a more detailed discussion of specific imaging modalities based upon the overall system architecture outlined in FIG. 2.

Figure 3:
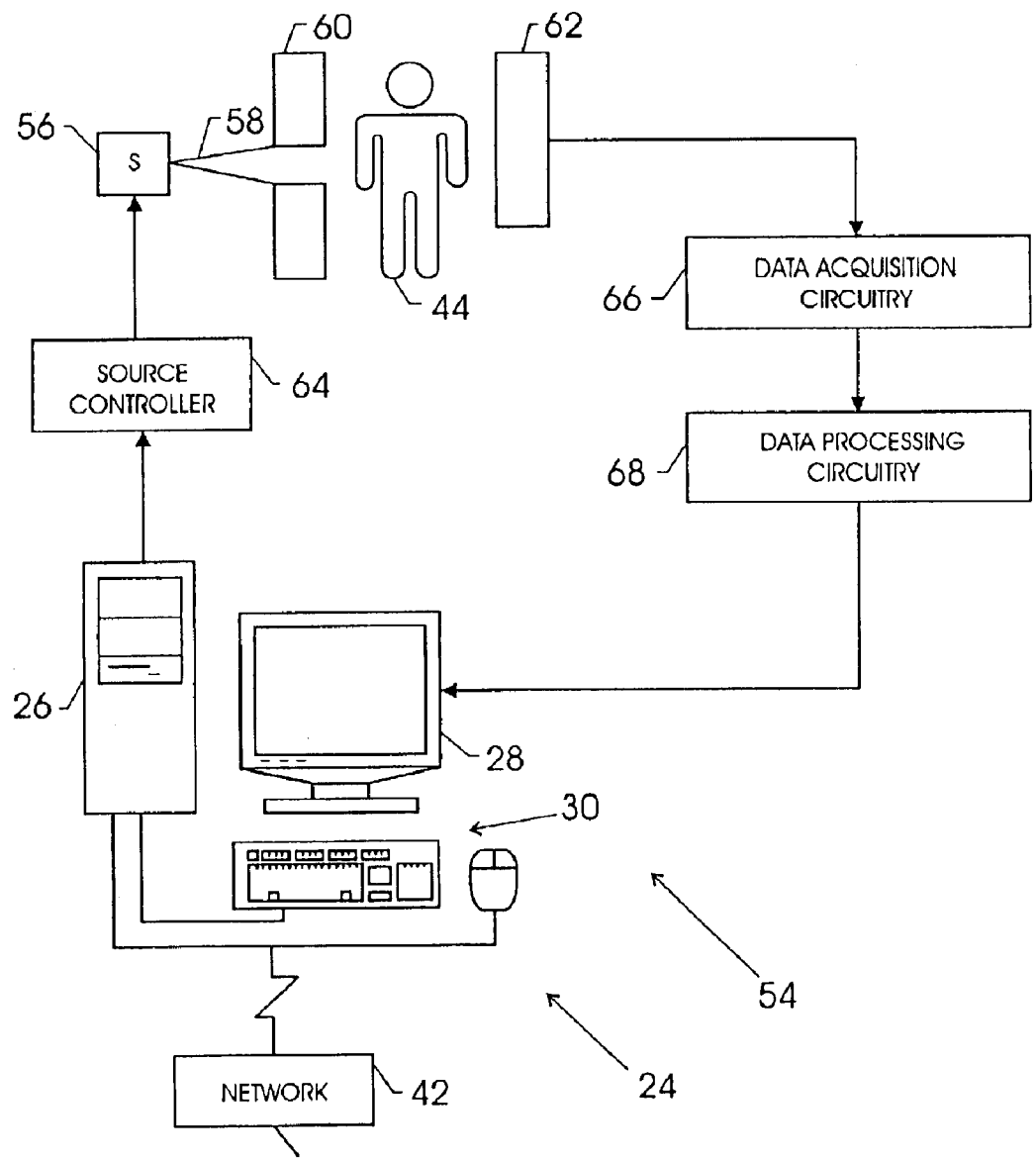
FIG. 3 is a diagrammatical representation of an exemplary X-ray imaging system equipped for automatic planned maintenance scheduling.

FIG. 3 generally represents a digital X-ray system 54. It should be noted that, while reference is made in FIG. 3 to a digital system, conventional X-ray systems may, of course, be provided as controllable and prescribable resources in the present technique. In particular, conventional X-ray systems may offer extremely useful tools both in the form of photographic film, and digitized image data extracted from photographic film, such as through the use of a digitizer.

System 54 illustrated in FIG. 3 includes a radiation source 56, typically an X-ray tube, designed to emit a beam 58 of radiation. The radiation may be conditioned or adjusted, typically by adjustment of parameters of the source 56, such as the type of target, the input power level, and the filter type. The resulting radiation beam 58 is typically directed through a collimator 60 which determines the extent and shape of the beam directed toward patient 44. A portion of the patient 44 is placed in the path of beam 58, and the beam impacts a digital detector 62.

Detector 62, which typically includes a matrix of pixels, encodes intensities of radiation impacting various locations in the matrix. A scintillator converts the high energy X-ray radiation to lower energy photons which are detected by photodiodes within the detector. The X-ray radiation is attenuated by tissues within the patient, such that the pixels identify various levels of attenuation resulting in various intensity levels which will form the basis for an ultimate reconstructed image.

Control circuitry and data acquisition circuitry are provided for regulating the image acquisition process and for detecting and processing the resulting signals. In particular, in the illustration of FIG. 3, a source controller 64 is provided for regulating operation of the radiation source 56. Other control circuitry may, of course, be provided for controllable aspects of the system, such as a table position, radiation source position, and so forth. Data acquisition circuitry 66 is coupled to the detector 62 and permits readout of the charge on the photodetectors following an exposure. In general, charge on the photodetectors is depleted by the impacting radiation, and the photodetectors are recharged sequentially to measure the depletion. The readout circuitry may include circuitry for systematically reading rows and columns of the photodetectors corresponding to the pixel locations of the image matrix. The resulting signals are then digitized by the data acquisition circuitry 66 and forwarded to data processing circuitry 68.

The data processing circuitry 68 may perform a range of operations, including adjustment for offsets, gains, and the like in the digital data, as well as various imaging enhancement functions. The resulting data is then forwarded to an operator interface or storage device for short or long-term storage. The images reconstructed based upon the data may be displayed on the operator interface, or may be forwarded to other locations, such as via network 42 for viewing. Also, digital data may be used as the basis for exposure and printing of reconstructed images on a conventional hard copy medium such as photographic film.

Figure 4:
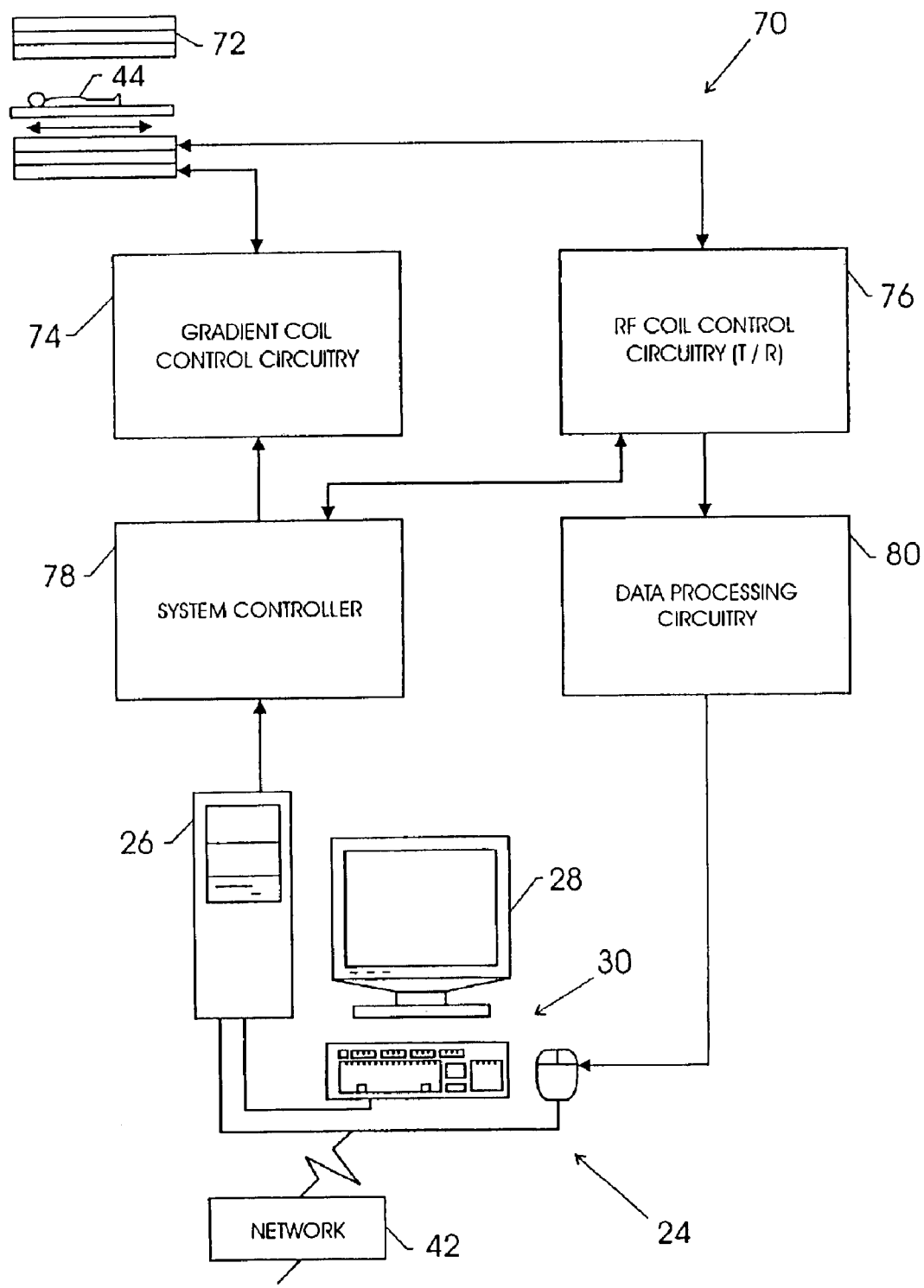
FIG. 4 is a diagrammatical representation of an exemplary magnetic resonance imaging system equipped for automatic planned maintenance scheduling.

FIG. 4 represents a general diagrammatical representation of a magnetic resonance imaging system 70. The system includes a scanner 72 in which a patient is positioned for acquisition of image data. The scanner 72 generally includes a primary magnet for generating a magnetic field which influences gyromagnetic materials within the patient's body. As the gyromagnetic material, typically water and metabolites, attempts to align with the magnetic field, gradient coils produce additional magnetic fields which are orthogonally oriented with respect to one another. The gradient fields effectively select a slice of tissue through the patient for imaging, and encode the gyromagnetic materials within the slice in accordance with phase and frequency of their rotation. A radio-frequency (RF) coil in the scanner generates high frequency pulses to excite the gyromagnetic material and, as the material attempts to realign itself with the magnetic fields, magnetic resonance signals are emitted which are collected by the radio-frequency coil.

The scanner 72 is coupled to gradient coil control circuitry 74 and to RF coil control circuitry 76. The gradient coil control circuitry permits regulation of various pulse sequences which define imaging or examination methodologies used to generate the image data. Pulse sequence descriptions implemented via the gradient coil control circuitry 74 are designed to image specific slices, anatomies, as well as to permit specific imaging of moving tissue, such as blood, and defusing materials. The pulse sequences may allow for imaging of multiple slices sequentially, such as for analysis of various organs or features, as well as for three-dimensional image reconstruction. The RF coil control circuitry 76 permits application of pulses to the RF excitation coil, and serves to receive and partially process the resulting detected MR signals. It should also be noted that a range of RF coil structures may be employed for specific anatomies and purposes. In addition, a single RF coil may be used for transmission of the RF pulses, with a different coil serving to receive the resulting signals.

The gradient and RF coil control circuitry function under the direction of a system controller 78. The system controller implements pulse sequence descriptions which define the image data acquisition process. The system controller will generally permit some amount of adaptation or configuration of the examination sequence by means of an operator interface 24.

Data processing circuitry 80 receives the detected MR signals and processes the signals to obtain data for reconstruction. In general, the data processing circuitry 80 digitizes the received signals, and performs a two-dimensional fast Fourier transform on the signals to decode specific locations in the selected slice from which the MR signals originated. The resulting information provides an indication of the intensity of MR signals originating at various locations or volume elements (voxels) in the slice. Each voxel may then be converted to a pixel intensity in image data for reconstruction. The data processing circuitry 80 may perform a wide range of other functions, such as for image enhancement, dynamic range adjustment, intensity adjustments, smoothing, sharpening, and so forth. The resulting processed image data is typically forwarded to an operator interface for viewing, as well as to short or long-term storage. As in the case of foregoing imaging systems, MR image data may be viewed locally at a scanner location, or may be transmitted to remote locations both within an institution and remote from an institution such as via network 42.

Figure 5:
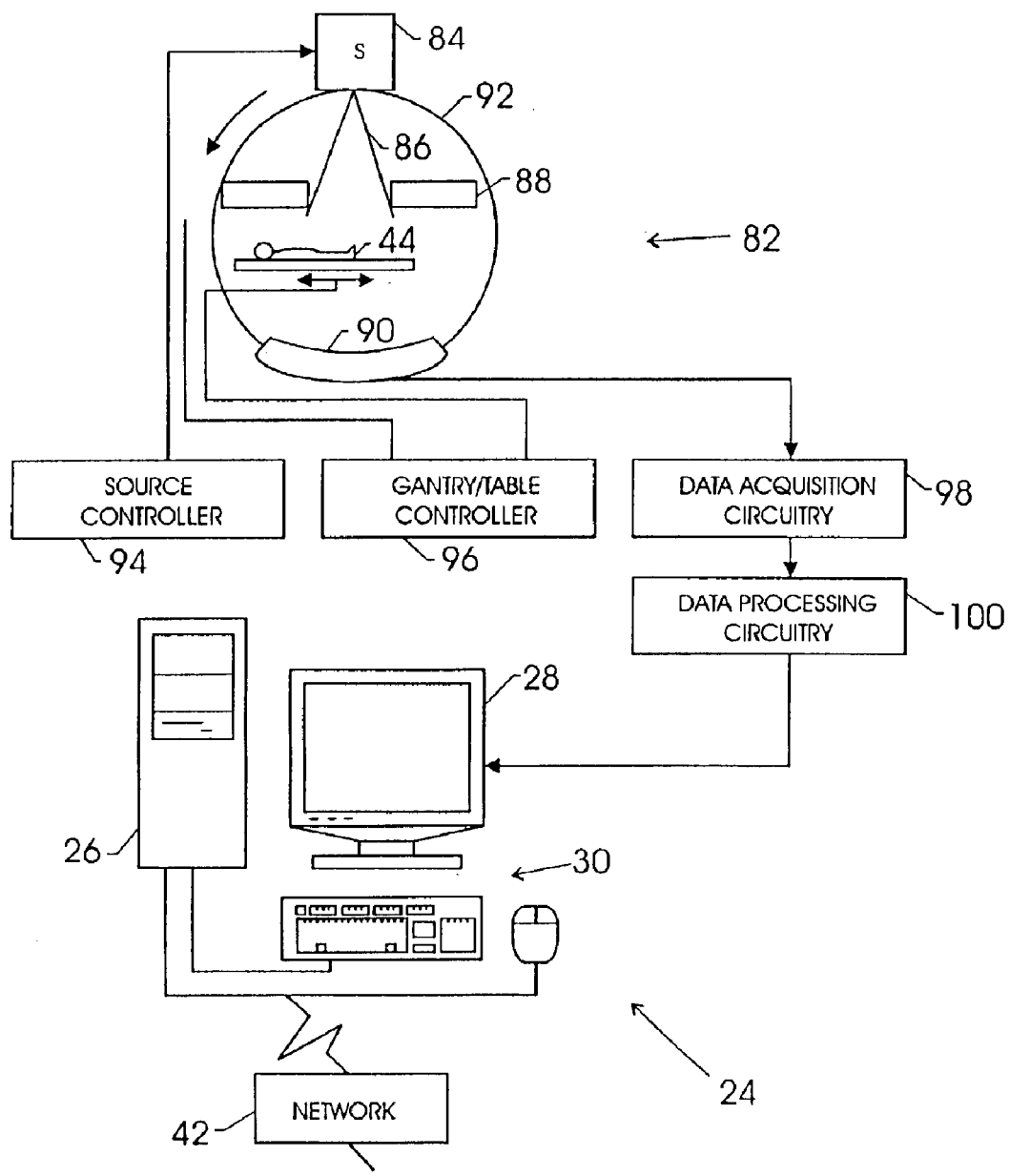
FIG. 5 is a diagrammatical representation of an exemplary computed tomography imaging system equipped for automatic planned maintenance scheduling.

FIG. 5 illustrates the basic components of a computed tomography (CT) imaging system. The CT imaging system 82 includes a radiation source 84 which is configured to generate X-ray radiation in a fan-shaped beam 86. A collimator 88 defines limits of the radiation beam. The radiation beam 86 is directed toward a curved detector 90 made up of an array of photodiodes and transistors which permit readout of charges of the diodes depleted by impact of the radiation from the source 84. The radiation source, the collimator and the detector are mounted on a rotating gantry 92 which enables them to be rapidly rotated (such as at speeds of two rotations per second).

During an examination sequence, as the source and detector are rotated, a series of view frames are generated at angularly-displaced locations around a patient 44 positioned within the gantry. A number of view frames (e.g. between 500 and 1000) are collected for each rotation, and a number of rotations may be made, such as in a helical pattern as the patient is slowly moved along the axial direction of the system. For each view frame, data is collected from individual pixel locations of the detector to generate a large volume of discrete data. A source controller 94 regulates operation of the radiation source 84, while a gantry/table controller 96 regulates rotation of the gantry and control of movement of the patient.

Data collected by the detector is digitized and forwarded to a data acquisition circuitry 98. The data acquisition circuitry may perform initial processing of the data, such as for generation of a data file. The data file may incorporate other useful information, such as relating to cardiac cycles, positions within the system at specific times, and so forth. Data processing circuitry 100 then receives the data and performs a wide range of data manipulation and computations.

In general, data from the CT scanner can be reconstructed in a range of manners. For example, view frames for a full 360° of rotation may be used to construct an image of a slice or slab through the patient. However, because some of the information is typically redundant (imaging the same anatomies on opposite sides of a patient), reduced data sets comprising information for view frames acquired over 180° plus the angle of the radiation fan may be constructed. Alternatively, multi-sector reconstructions are utilized in which the same number of view frames may be acquired from portions of multiple rotational cycles around the patient. Reconstruction of the data into useful images then includes computations of projections of radiation on the detector and identification of relative attenuations of the data by specific locations in the patient. The raw, the partially processed, and the fully processed data may be forwarded for post-processing, storage and image reconstruction. The data may be available immediately to an operator, such as at an operator interface 24, and may be transmitted remotely via network 42.

Figure 6:
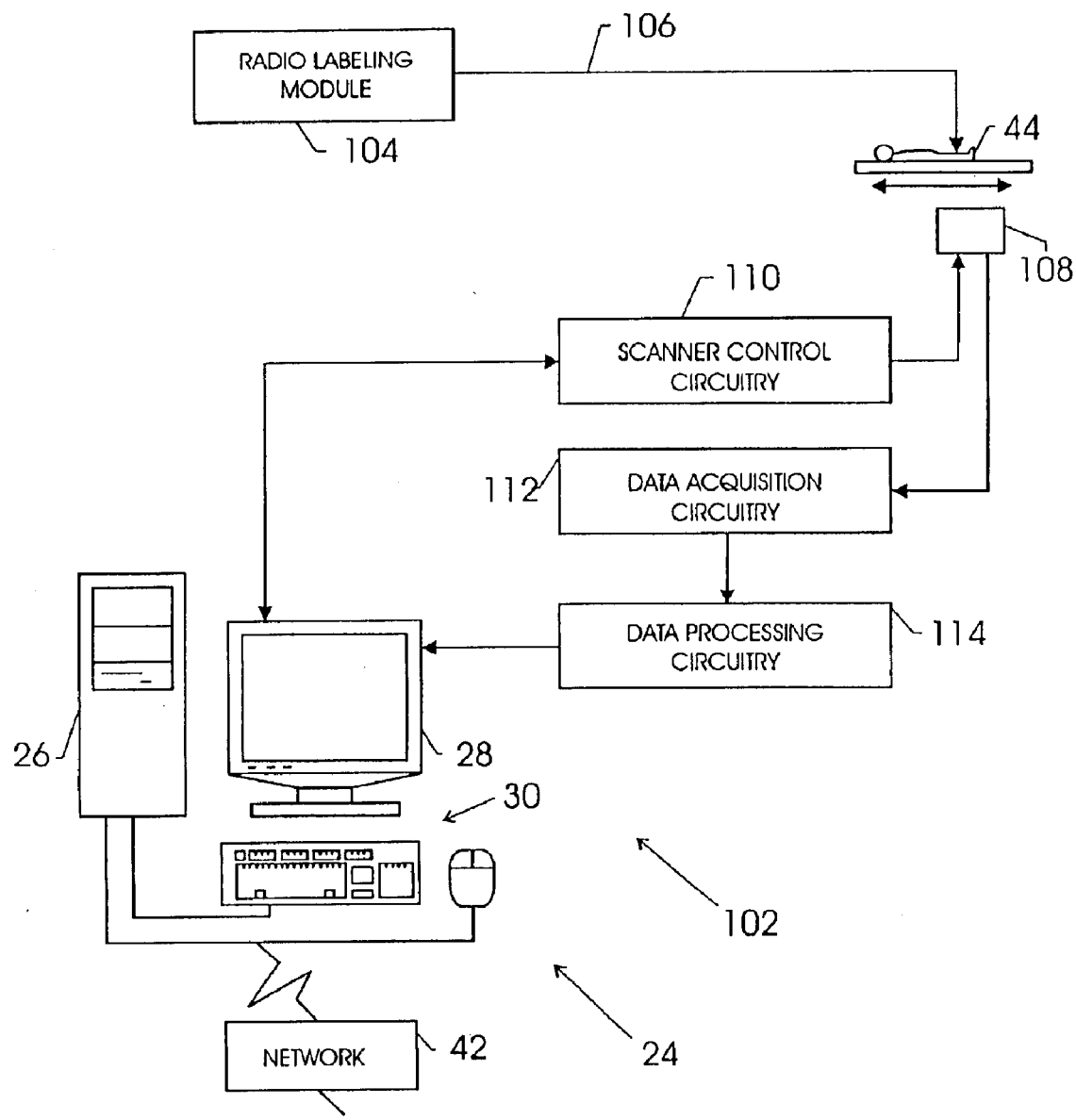
FIG. 6 is a diagrammatical representation of an exemplary positron emission tomography system equipped for automatic planned maintenance scheduling.

FIG. 6 illustrates certain basic components of a positron emission tomography (PET) imaging system. The PET imaging system 102 includes a radio-labeling module 104 which is sometimes referred to as a cyclotron. The cyclotron is adapted to prepare certain tagged or radio-labeled materials, such as glucose, with a radioactive substance. The radioactive substance is then injected into a patient 44 as indicated at reference numeral 106. The patient is then placed in a PET scanner 108. The scanner detects emissions from the tagged substance as its radioactivity decays within the body of the patient. In particular, positrons, sometimes referred to as positive electrons, are emitted by the material as the radioactive nuclide level decays. The positrons travel short distances and eventually combine with electrons resulting in emission of a pair of gamma rays. Photomultiplier-scintillator detectors within the scanner detect the gamma rays and produce signals based upon the detected radiation.

The scanner 108 operates under the control of scanner control circuitry 110, itself regulated by an operator interface 24. In most PET scans, the entire body of the patient is scanned, and signals detected from the gamma radiation are forwarded to data acquisition circuitry 112. The particular intensity and location of the radiation can be identified by data processing circuitry 114, and reconstructed images may be formulated and viewed on operator interface 24, or the raw or processed data may be stored for later image enhancement, analysis, and viewing. The images, or image data, may also be transmitted to remote locations via network 42.

PET scans are typically used to detect cancers and to examine the effects of cancer therapy. The scans may also be used to determine blood flow, such as to the heart, and may be used to evaluate signs of coronary artery disease. Combined with a myocardial metabolism study, PET scans may be used to differentiate non-functioning heart muscle from heart muscle that would benefit from a procedure, such as angioplasty or coronary artery bypass surgery, to establish adequate blood flow. PET scans of the brain may also be used to evaluate patients with memory disorders of undetermined causes, to evaluate the potential for the presence of brain tumors, and to analyze potential causes for seizure disorders. In these various procedures, the PET image is generated based upon the differential uptake of the tagged materials by different types of tissue.

Figure 7:
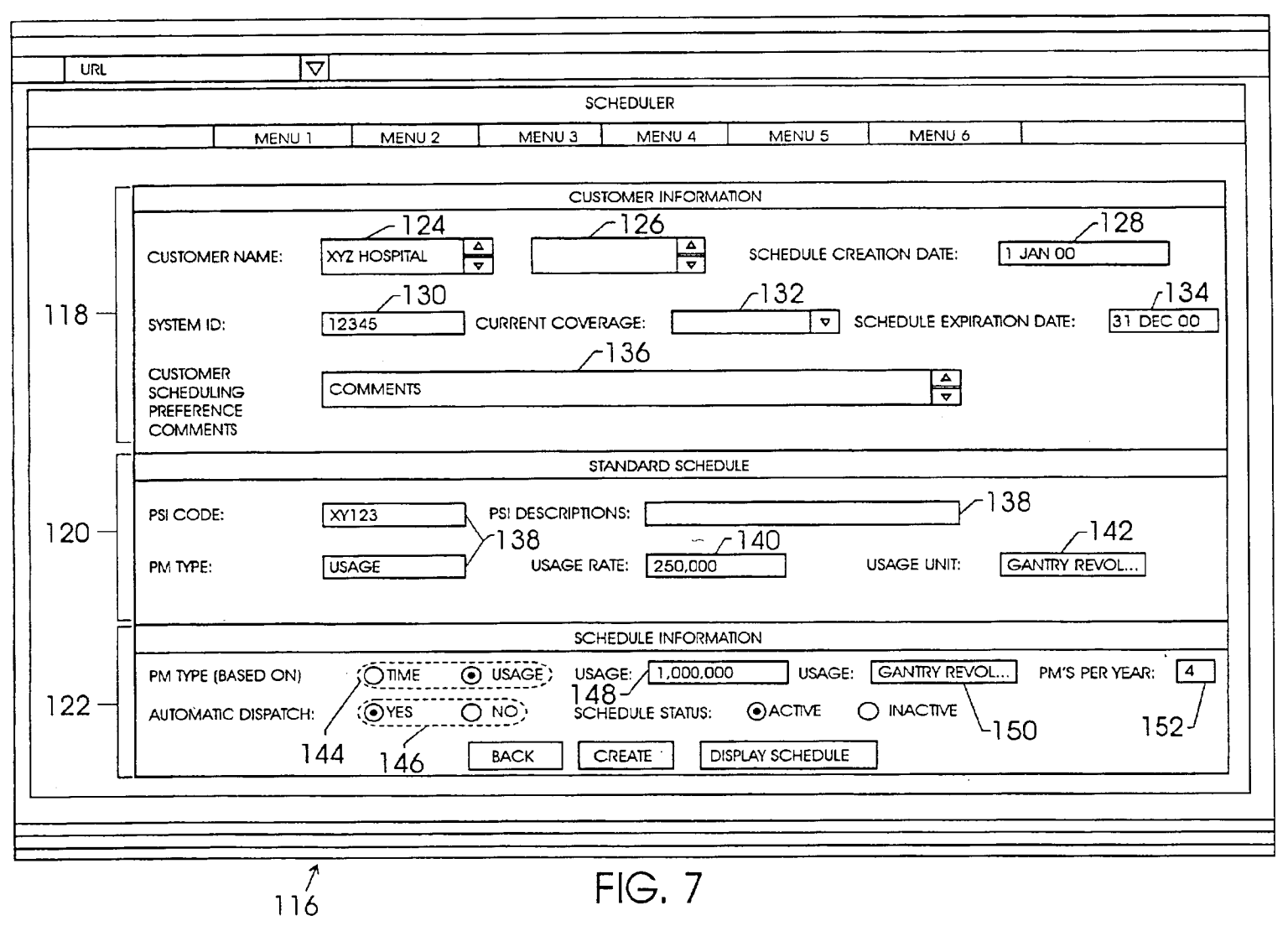

As noted above, the present technique permits automated and customized scheduling of planned maintenance for systems of various types as illustrated in FIGS. 2–6, in addition to other system types as well. The scheduling may be set in accordance with specific requirements or desires of individual institutions or field engineers, and managed in various ways. In a present embodiment, a series of user viewable interface screens or pages may be presented, as illustrated in FIG. 7 to facilitate viewing scheduling parameters and altering the parameters to match such needs and desires. The pages may be viewed on field engineer stations 22 (see FIG. 1), interface stations 24 at the maintained systems themselves, or at any other suitable location. Appropriate access controls and permissions may, of course, be put into place to limit access to the pages, as well as alteration of the system settings.

The exemplary interface page of FIG. 7, designated generally by reference numeral 116, includes a system identification section 118, a planned maintenance scheduling section 120, and a planned maintenance selection section 122. Section 118 permits viewing and setting of various identifying information for specific maintained systems, such as a customer name field 124, and a field engineer or contact identification field 126. In the illustrated example, a schedule creation date field 128 if also provided. Additional, system-specific identification information may be provided in field 130. A coverage field 132 may be used to enter or select a type of service contract or arrangement under which the scheduled maintenance is provided. Field 134 provided an indication of the expiration data of any such arrangement or of the schedule created as indicated in field 128. Finally section 118, in the illustrated embodiment, provides a field for input of customer scheduling preferences or comments.

Scheduling section 120 provides for certain settings related to the overall scheme of servicing of the equipment identified in section 118. For example, "PSI" or product family code, product family description, and planned maintenance type fields allow for identification of an equipment type and planned maintenance type. The equipment type identification may be used for determining appropriate scheduling of maintenance by comparison of the prepared schedule with schedules for other equipment of similar types. Similarly, when maintenance is performed on a usage basis, the product family code field may offer a basis for determining whether usage, downtime, or particular problems experienced with the serviced equipment is within or outside certain norms for similar equipment. The planned maintenance field, illustrated as set to "usage" in FIG. 7, may alternatively be set to "time" for computation of maintenance schedules on an interval basis.

A usage rate field 140 provides for specifying a reference usage value for planned maintenance, while a usage unit field 142 provides an indication of the units to be used for planning usage-based maintenance. In a present implementation, the reference usage value is set for each equipment type, such as by imaging modality. The value may be based upon prior knowledge, empirical data, estimates by qualified technicians or designers, or by any other means. The usage units are similarly set, as described above, for a parameter that provides a direct or indirect indication of needs for maintenance based upon usage.

As noted above, the present technique provides a high degree of customization of planned maintenance on both timed and usage bases. Planned maintenance selection section 122 allows parameters defining such customization to be set. A first selection 144, therefore, allows for selection of timed or usage-based planned maintenance. When timed scheduling is selected, the system may compute maintenance based upon service intervals alone. As described below, however, by selecting usage-based planned maintenance, the system executes routines for accessing and converting data relating to operational parameters of the serviced equipment, and projects needed maintenance based upon the actual usage. An automatic dispatch selection 146 may also be provided. Depending upon the units upon which usage-based maintenance is calculated, a usage rate value may be input into field 148. The particular units or parameter on which the usage rate value is based may then be specified in field 150. The resulting number of scheduled maintenance sessions may then be set or computed as set forth below, and viewed in a field 152. As will be appreciated by those skilled in the art, certain of the fields in section 122 may be open to user specification, or specific settings or selections may be provided, such as in pull-down menus, lists, or the like.

Figure 8:
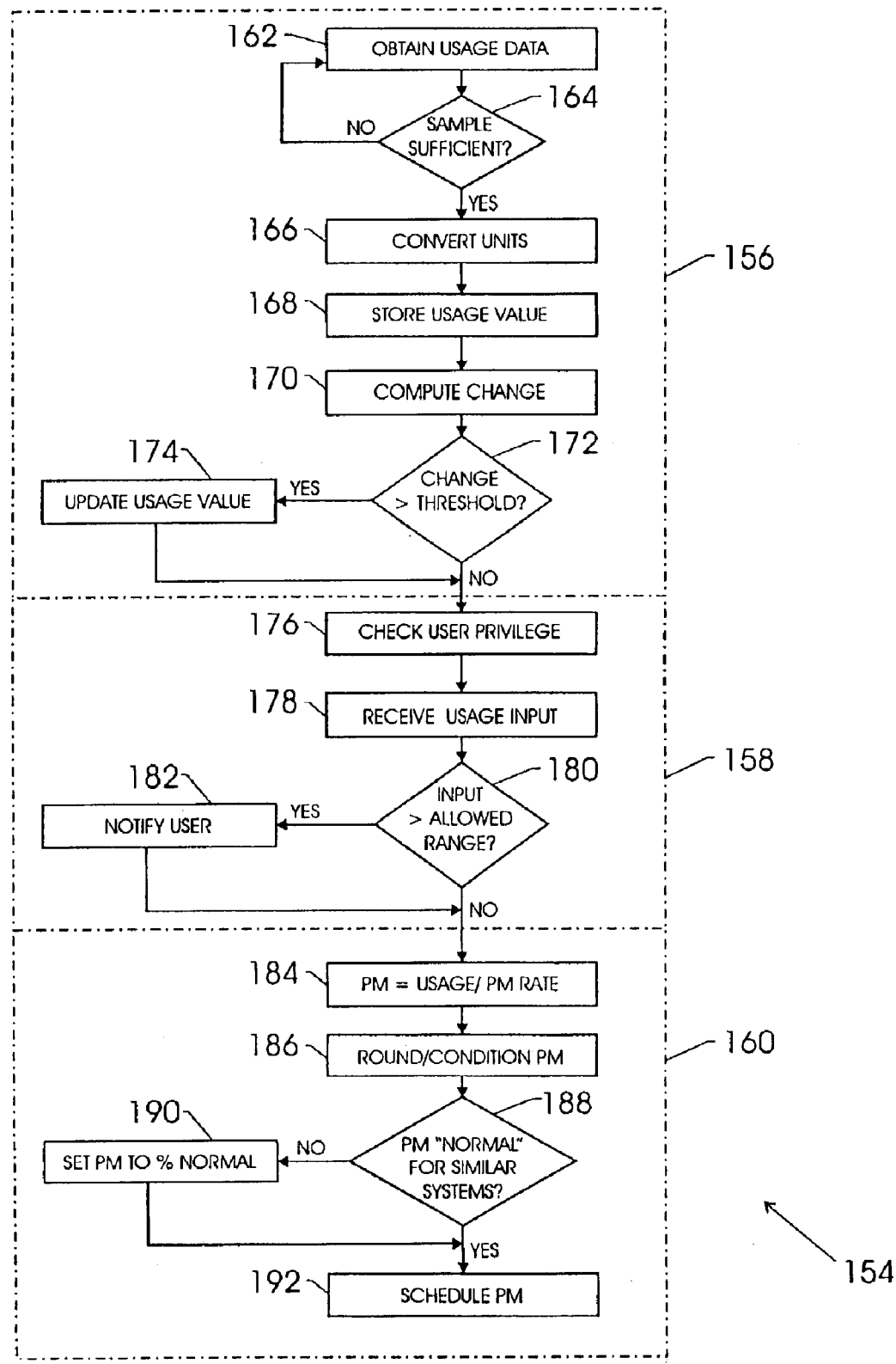
FIG. 8 is a flow chart illustrating exemplary control logic for setting usage values and computing planned maintenance schedules in accordance with the present technique.

FIG. 8 represents exemplary steps in usage-based maintenance scheduling logic implemented by system 10 in accordance with the present technique based upon inputs obtained through an interface such as that shown in FIG. 7. The logic, designated generally by the reference numeral 154, may be considered to include three sections or general functions, including data collection logic 156, manual setting/override logic 158, and scheduling logic 160. More of somewhat different particular steps and functionalities may, of course, be provided in specific implementations.

The data collection logic 156 begins at step 162 in which usage data is obtained. The usage data may include any desired type of parameters that can form the basis for determining when maintenance should be scheduled. Through the present discussion, for example, it will be assumed that service is to be provided to a CT imaging system based upon revolutions of a gantry assembly. Periodically, then the system will be polled, or may automatically report, data indicative of gantry revolutions. At step 164 the logic determines whether a sufficient sample has been obtained to proceed. In particular, because the technique is automated and automatically adapts based upon changing heavy or light usage to update of change maintenance schedules, too small a sample may provide an uncharacteristic high or low projection of usage. Over larger samples, on the other hand, reliability of the data in providing an accurate view of usage and usage trends can be obtained.

At step 166 the data collected is converted to the desired usage basis units, if required. For example, continuing the example of gantry revolutions in a CT imaging system, data directly indicating gantry revolutions may not be available, while other parameters, such as slice counts, may provide an indirect indication of revolutions. At step 166, then, such data is converted to the desired units. A resulting usage value, reflecting the rate of usage in the desired units normalized over the sample period, is then stored as indicated at step 168.

At step 170, the current usage value is compared with a previously stored usage value, and the difference is compared to a threshold to determine whether usage is increasing or decreasing to such a degree as to necessitate a change in maintenance scheduling. For example, in a present implementation a threshold of 5% indicates that a new usage value should be the basis for forward-going scheduling. If the comparison is affirmative, the new usage value is stored as the basis for future comparisons, as indicated at step 174.

Logic 158, then, allows certain settings to be manually made, or defaults or calculated values to be overridden, such as based upon input via an interface page of the type illustrated in FIG. 7. At step 176 user privileges are first checked to verify that the user is authorized to make such changes. At step 178 the user input is received, as from the interface page-based fields. The user may specify various usage-based parameters for the basis of maintenance scheduling, such as the usage rate value (see field 148 in FIG. 7), the basis for usage evaluation (see field 150 in FIG. 7), and so forth. At step 180 the logic determines whether the user input is within certain prescribed ranges, such as to prevent maintenance from being scheduled at intervals that are too long or brief. Where desired, comparisons may be made at this point to typical or design servicing needs for similar equipment, such as by reference to the product family code or similar information (see field 138 in FIG. 7). Similarly, absent some manual setting or override, such settings may be made by default based upon empirical data or updated data derived from actual performance of similar systems. If the input is outside the range, a notice may be given to the user at step 182 and the input may be accepted or rejected by the system, or the user may simply be prompted to input a different value within the allowable range.

With the usage value and range set, the logic proceeds to step 184, where the planned maintenance timing is developed. In particular, based upon the reference usage value (e.g. number of gantry revolutions) and the usage rate value, the projected number of planned maintenance sessions per unit time (e.g. per year) is computed. In a present implementation, the number of sessions is obtained by dividing the usage rate value by the reference usage value. Other algorithms may, of course, be provided for this calculation, where appropriate. At step 186 the number of sessions can be rounded or otherwise filtered or conditioned. In a present implementation, for example, when the fractional portion of the computed number of maintenance sessions exceeds 0.2, the next higher integer number of sessions on an annualized basis is adopted.

At step 188, the logic determines whether the resulting number of planned maintenance sessions is "normal" for similar systems. Again, this comparison may be based upon preset values, but is preferably associated with the particular equipment type, as indicated by the product family code (see field 138 in FIG. 7). If the number of sessions is lower than the norm, the number is reset to some other value, as indicated at step 190. Steps 188 and 190 may thereby serve to ensure that some minimum number of maintenance sessions is set regardless of low usage. Similar adjustments may be made on other bases. Finally at step 192 the planned maintenance schedule is set by casting the prescribed number of sessions over a desired period (e.g. annually) beginning as a desire date (e.g. the date of calculation of the schedule).

A number of convenient improvements are embodied in the logic set forth in FIG. 8. For example, the technique permits selection of time-based or usage-based maintenance scheduling. Moreover, when based upon usage, the scheduling function may track changing usage and automatically update the maintenance schedule as usage increased or decreases. Further, the usage-based scheduling may be informed by data for usage or maintenance needs of similar equipment.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for scheduling maintenance of imaging systems comprising:

accessing operational data collected from an imaging system;

identifying a trend in usage of the system based upon the operational data and updating usage data based upon the identified trend; and calculating a planned maintenance schedule based upon the usage data and upon a reference usage value.

2. The method of claim 1, comprising determining whether the operational data accessed represents a sufficient sample of operational data for identification of the trend.

3. The method of claim 1, wherein further comprising collecting the operational data from the system via a network link.

4. The method of claim 1, wherein the usage value is set by an operator via an interface page.

5. The method of claim 4, comprising verifying that the usage value is within a desired range for a desired usage unit, and providing an operator notification if the usage value is outside the desired range.

6. The method of claim 1, wherein the planned maintenance schedule is based upon a number of maintenance sessions in a desired time period, the number of maintenance sessions being computed based upon the usage data and the reference usage value.

7. The method of claim 6, comprising rounding the number of maintenance sessions to an integer value for the desired time period.

8. The method of claim 1, comprising determining whether a frequency of maintenance defined by the schedule is normal for an equipment type characteristic of the system.

9. A method for scheduling maintenance of imaging systems comprising:

selecting time-based or usage-based planned maintenance scheduling;

if time-based scheduling is selected, computing a maintenance schedule based upon a desired maintenance interval;

if usage-based scheduling is selected, accessing usage data for an imaging system, and calculating a planned maintenance schedule based upon the usage data and upon a reference usage value.

10. The method of claim 9, comprising identifying a trend in usage of the system based upon the usage data and previous usage data for the system, wherein if usage-based scheduling is selected, the planned maintenance schedule is calculated based upon the trend.

11. The method of claim 10, wherein the planned maintenance schedule is calculated based upon most current usage data.

12. The method of claim 10, comprising determining whether the usage data represents a sufficient sample for identification of the trend.

13. A method for scheduling planned maintenance for imaging systems comprising:

collecting operational data from a plurality of imagining systems via a network;

converting the operational data to usage data for parameters of interest;

calculating a usage-based planned maintenance schedule for each imaging system based upon the respective usage data and respective reference usage values for the parameters of interest.

14. The method of claim 13, wherein the imaging systems are of different imaging modality, and the parameter of interest is selected based upon the respective imaging modality.

15. The method of claim 14, wherein the modalities are selected from a group consisting of magnetic resonance imaging systems, X-ray imaging systems, computed tomography imaging systems and positron emission tomography systems.

16. The method of claim 13, wherein the reference usage values are set independently for each system.

17. A system for scheduling maintenance of imaging systems comprising:
   a communications module configured to establish a network connection with a plurality of imaging systems via a network;
   a data collection module configured to access operational data from the imaging systems via the network; and
   a planned maintenance scheduling module configured to calculate a planned maintenance schedule based upon the respective operational data for each system and upon reference usage values.

18. The system of claim 17, further comprising a field engineer station configured to display an interface page for inputting at least one parameter on which the maintenance schedule is calculated.

19. The system of claim 17, further comprising a conversion module for converting the operational data to desired units that serve as a basis for calculating the maintenance schedule.

20. A system for scheduling maintenance of imaging systems comprising:
   means for accessing operational data collected from an imaging system;
   means for identifying a trend in usage of the system based upon the operational data and updating usage data based upon the identified trend; and
   means for calculating a planned maintenance schedule based upon the usage data and upon a reference usage value.

21. A system for scheduling planned maintenance for imaging systems comprising:
   means for collecting operational data from a plurality of imaging systems via a network;
   means for converting the operational data to usage data for parameters of interest;
   means for calculating a usage-based planned maintenance schedule for each imaging system based upon the respective usage data and respective usage reference values for the parameters of interest.

22. A computer program for scheduling maintenance of imaging systems comprising:
   a computer readable medium configured to store machine executable code; and
   a computer program stored on the medium, the program comprising executable routines for accessing operational data collected from an imaging system, identifying a trend in usage of the system based upon the operational data and updating usage data based upon the identified trend, and calculating a planned maintenance schedule based upon the usage data and upon a reference usage value.

23. A computer program for scheduling maintenance of imaging systems comprising:
   a computer readable medium configured to store machine executable code; and
   a computer program stored on the medium, the program comprising executable routines for permitting selection time-based or usage-based planned maintenance scheduling, and if time-based scheduling is selected, computing a maintenance schedule based upon a desired maintenance interval, and if usage-based scheduling is selected, accessing usage data for an imaging system, and calculating a planned maintenance schedule based upon the usage data and upon a reference usage value.

24. A computer program for scheduling maintenance of imaging systems comprising:
   a computer readable medium configured to store machine executable code; and
   a computer program stored on the medium, the program comprising executable routines for collecting operational data from a plurality of imaging systems via a network, converting the operational data to usage data for parameters of interest, calculating a usage-based planned maintenance schedule for each imaging system based upon the respective usage data and respective reference usage values for the parameters of interest.

* * * * *